United States Patent [19]
Holthuis et al.

[11] Patent Number: 5,760,039
[45] Date of Patent: Jun. 2, 1998

[54] LYOPHILIZED COMPOSITION CONTAINING S(+)-4,4'-(1-METHYL-1,2-ETHANEDIYL)-BIS(2,6-PIPERAZINEDIONE)

[75] Inventors: Josephus J. M. Holthuis, Leiden; Alwinus A. Voetman, Zwanenburg, both of Netherlands

[73] Assignee: Chiron Corporation, Emeryville, Calif.

[21] Appl. No.: 827,676

[22] Filed: Apr. 10, 1997

Related U.S. Application Data

[63] Continuation of Ser. No. 211,974, filed as PCT/EP92/02400, Oct. 22, 1992 published as WO93/07873, Apr. 29, 1993, abandoned.

[30] Foreign Application Priority Data

Oct. 25, 1991 [GB] United Kingdom ............... 9122720

[51] Int. Cl.$^6$ ............... C07D 403/02; A61K 31/495
[52] U.S. Cl. ............... 514/252; 544/357
[58] Field of Search ............... 544/357; 514/252

[56] References Cited

U.S. PATENT DOCUMENTS 3,941,790  3/1976  Creighton ............... 544/357
4,963,551  10/1990  Palepu ............... 514/252

FOREIGN PATENT DOCUMENTS

| 0 284 594 | 9/1988 | European Pat. Off. . |
| 0 409 499 | 1/1991 | European Pat. Off. . |
| 1 234 935 | 6/1971 | United Kingdom . |

OTHER PUBLICATIONS

Martindale, The Extra Pharmacopoeia, Twenty–eighth Edition (1982) p. 225.
Repta A., et al., *J. of Pharm. Sciences* (1976) 65(2):238–242.
Martindale, *The ExtraPharmacopoeia*, 28th edition, The Pharmaceutical Press, London (1982).

*Primary Examiner*—Matthew V. Grumbling
*Attorney, Agent, or Firm*—Robert P. Blackburn

[57] ABSTRACT

A process of making a stable lyophilized, white to off-white, crack-free preparation of ICRF-187 in which the cake of ICRF-187 is protected against the deleterious effect of light, has a moisture content of not more than about 2% wherein the process comprises lyophilization using a starting solution of a therapeutically acceptable acid salt of ICRF-187 having a concentration of up to about 25 mg/ml and in which the primary drying stage lasts at least 30 hours, preferably at least 40 hours, and/or uses a primary drying temperature of from about 30° C. to about 40° C.

12 Claims, No Drawings

LYOPHILIZED COMPOSITION CONTAINING S(+)-4,4'-(1-METHYL-1,2-ETHANEDIYL)-BIS(2,6-PIPERAZINEDIONE)

This application is a continuation of application Ser. No. 08/211,974, filed Aug. 1, 1994, abandoned, which is a 371 of PCT/EP92/02400, filed Oct. 22, 1992, from priority Great Britain, No. 9122720.7, filed Oct. 25, 1991.

This invention relates to an improved process for preparing lyophilized (S) (+)-4,4'-(1-methyl-1,2-ethanediol)-bis (2,6-piperazinedione) (hereinafter referred to as "ICRF-187") salts, and further provides new lyophilized preparations of these substances and therapeutic formulations preparable by reconstitution of such preparations. The invention is also concerned with new findings on light stability of ICRF-187 salts, and solutions thereof.

ICRF-187 was described by creighton in, inter alia, U.S. Pat. No. 3,941,790 as a material useful for aiding regression and palliation of cancer in mammals. In Pathologie Biologie, 1987, 35 (No 1) 49–53, Green described how certain anthracyclines are effective anti-tumour agents but carry the side effect of a tendency to produce cardiotoxicity upon chronic administration. Green, however, also disclosed for the first time that ICRF-187 could protect against such cardiotoxicity. One particular widely used anti-cancer drug suffering from the disadvantage of associated cardiotoxicity is doxorubicin hydrochloride. In U.S. Pat. No. 4,963,551, Palepu at al described a method of formulating ICRF-187 in a manner stated as facilitating intravenous (I.V.) administration of this substance (and the manufacture of an I.V. product) as a cardioprotective agent to reduce or prevent cardiotoxicity resulting from the administration of doxorubicin hydrochloride.

As for the manufacture of ICRP-187 Creighton, supra, essentially described two methods. In the first method, 1,2-diaminopropane tetraacetic acid is heated with formamide to result in incorporation of nitrogen and ring closure. In the second method, the tetraamide corresponding to the above tetraacid is heated in polyphosphoric acid or phenol, bringing about cyclization.

U.S. Pat. No. 4,764,614 describes an alternative synthesis in which propylenediamine tetraadetic acid tetraatide is treated in a dipolar aprotic solvent with an alkali metal derivative of dinethyl sulfoxide to form a dialkali metal salt of the desired bis-piperazinedione, the desired heterocyclic product.

EP-A-O 330 381 describes yet an alternative process for preparing, inter alia, ICRF-187 in which a corresponding tetranitrile is synthesized by reacting an appropriate diamine with formaldehyde and an alkali metal cyanide. The tetranitrile is then hydrated to yield an acid addition salt of the corresponding tetraanide, and this latter substance may then be cyclized.

In Repta et al, J. Pharmaceutical Sciences, 65(No 2) 238–242, the tetraacid product is synthesized from 1,2-diaminopropane dihydrochloride by reaction with chloroacetic acid and sodium hydroxide, and removal of salt byproduct is achieved using a cation-exchange resin column operated at elevated temperature. This technique is, however, very cumbersome, and quite impractical for industrial scale operation.

Attempts at the separation of alkali metal salt and tetraacid product by fractional crystallization have resulted in significant product loss and consequent low overall yield of ICRF-187. Moreover, using alternative precipitation techniques for tetraacid isolation, an unprocessable gel often results from precipitating tetraacid product in the presence of alkali metal salt when using an organic solvent/water mix to achieve precipitation.

In a co-pending application filed today in the names of EuroCetus BV and sicor Limited, a copy of the specification of which is annexed hereto, a process is described for the preparation of ICRF-187 in which an intermediate 1,2-diaminopropane tetraacetic acid product is synthesized together with byproduct alkali metal salt, characterized in that the tetraacetic acid intermediate product is subjected to ring formation in the form of a crude product having substantial amounts of alkali metal salt thereby to produce the desired ICRF-187.

The formulations described in U.S. Pat. No. 4,963,551, supra, are stated to contain up to about 6% moisture, and yet be capable of being stored at room temperature. The specific embodiment described in U.S. Pat. No. 4,963,551 is of a lyophilized preparation in which the cake of lyophilizate appears pink and glossy with cracks. This cake is stated to contain about 6% moisture. It is acknowledged in U.S. Pat. No. 4,963,551, that the presence of more than 2% moisture in the lyophilizate will result in the formation of crystals. The prior art is, however, entirely silent on the effect of moisture on product decomposition and the effect of UV light on stability, and the effect of these influences in combination.

The lyophilization process of U.S. Pat. No. 4,963,551 has a relatively short primary drying time at a relatively low temperature. Including time under vacuum without heating, the primary drying stage in this prior art process lasts 23 hours, and the product temperature at the end of this stage is 10° C. We have now found that an appreciably higher drying temperature and/or a primary drying stage in which the time under heating is at least 30 hours (preferably 40 hours or more) and/or a secondary drying time in which the time under heating is no greater than 24 hours produces a product which contains appreciably less moisture, contains fewer color-causing impurities and decomposition products, and which is therefore more acceptable clinically. The present invention is also based upon the discoveries that ICRF-187 salts are light sensitive, and are far more unstable in the presence of appreciable moisture content.

We have also found that a clinically satisfactory product, lacking appreciable evidence of colored decomposition products, dictates a limit to the concentration of the bulk solution from which the present lyophilized preparation is made. U.S. Pat. No. 4,963,551 states that the preparation described therein is made from a bulk solution having a minimum content of ICRF-187 of 25 mg/ml, and even suggests an upper limit as high as 40 mg/ml. We have found that the production of a more satisfactory cake lacking the clinically unsatisfactory pink and glossy characteristics and cracking described in this prior art sets an upper limit of concentration on the bulk solution which is certainly no higher than 25 mg/ml, and preferably no higher than about 20 mg/ml.

Accordingly, in one aspect the present invention provides a stable lyophilised preparation of ICRF-187 in which the cake of ICRF-187 is protected against the deleterious effect of UV light, has a moisture content of not more than about 2%, preferably not more than about 1%, and is obtainable by a lyophilization process using a starting solution of ICRF-187 having a concentration of up to about 25 mg/ml and in which the primary drying stage lasts at least 30 hours, preferably at least 40 hours, and/or the primary drying temperature rapidly increases to a level of from about 30° C. to about 40° C. and/or the secondary temperature is from about 30° C. to about 40° C.

Our experiments have shown that ICRF-187 is very sensitive to decomposition in the presence of water. During the sublimation period of the lyophization process (primary drying), if the temperature is raised too fast coloration of the cake is observed (coloration of a white cake always points at decomposition). In addition to this, a fast rise in temperature (during primary drying) can result in melting of the frozen ice and/or collapse of the cake structure, which results in a deformed cake and a high residual water content. We have found, however, that when a relatively long period of primary drying and in most cases secondary drying are followed, a white product and an intact cake is obtained.

Several other parameters during the freeze drying process are of importance. The freezing time is not, however, critical. The primary drying can generally start as soon as the product temperature is −50° C. The sublimation period is important as noted above. The secondary drying stage commences when the product temperature equals the plate temperature, and its length is controlled by the pressure rise step.

The primary drying stage lasts at least 30 hours, preferably 40 to 50 hours, but it may exceed 50 hours. For example, if the drying temperature is only about 10° C. (as in the prior art process of U.S. Pat. No. 4963551), a primary drying time of 60 to 75 hours is appropriate. It will be appreciated that drying times during a lyophilization process are, in part, dictated by the size and nature of the equipment used. We have found that the number of vials employed, and altering the concentration of the starting ICRF-187 solution do not alter the timing. However, those of skill in the art will appreciate that increasing vial size and/or reducing the amount of solution in the vial prior to lyophilization reduces the required time period. Decreasing drying temperature, however, dictates a longer primary drying process in the present invention, and usually suggests a secondary drying stage of at least 10 hours, perhaps 15 to 25 hours. In U.S. Pat. 4,963,551, 100 cc vials were filled for the lyophilization of bulk solution, and a temperature of 10° C. was used for primary drying. Nonetheless the primary drying stage lasted only 23 hours, and overall drying lasted only 43 hours including the secondary drying stage.

The following Table 1 sets out preferred parameters for the present process, and shows the alterations in those parameters which apply on changing vial size/arrangement or temperature. Given the relatively lengthy primary drying process envisaged in the present invention, it may transpire that no secondary drying period at all is required. In any event it is usually no greater than about 25 hours. Generally, it is also preferred to operate with a secondary drying temperature of from about 30° C. to about 40° C. As an illustration of changes in secondary prying, operating under conditions where 100 ml vials loaded with half the original volume, the secondary drying period can be reduced to 80% of the original period, all other conditions remaining the same.

TABLE 1

| Operating conditions (b to f showing changes in a) | Freezing | Pr. Drying | Sec. Drying |
|---|---|---|---|
| a) Vial 36 ml 20 mg/ml N = 4000 | 1–2 hrs | 41–52 hrs | 16–25 hrs |
| Product end temp | −45°– −54° C. | 32–38° C. | 32–38° C. |
| Shelf temp | constant | 13° C./hr | constant |

TABLE 1-continued

| Operating conditions (b to f showing changes in a) | Freezing | Pr. Drying | Sec. Drying |
|---|---|---|---|
| ramp | | from −45° to +35° C. | |
| b) Number of vials twice as at a) | No changes | (within limits in a) | (within limits in a) |
| c) conc. 25 mg/ml | No changes | (within limits in a) | (within limits in a) |
| d) Vial of 100 ml | Reduction of time by 70% | Recution of time by 80% | Reduction of time by 50% |
| e) Same vial only 50% of fill volume of a) | Reduction of time by 50% | Reduction of time by 40% | Reuction of time by 20% |
| f) as a) except lower temperatures for drying stages | 1–2 hrs −45°– −54° C. | Increase of time by 50% → 60–75 hrs at 10° C. | Increase of of time by 15% → 19–28 hrs at 28° C. |

Accordingly, in another aspect, the present invention provides a process for preparing a lyophilizate of ICRF-187, which comprises lyophilizing a bulk solution of ICRF-187 of concentration no greater than about 25 mg/ml using a primary drying stage of duration at least about 30 hours and/or a primary drying temperature of from about 30° C. to about 40° C., and a secondary drying stage of no greater than about 25 hours. Preferably, the starting bulk solution concentration is no greater than about 20 mg/ml.

It will be appreciated that in Table 1 above the timings and percentage increases/decreases are approximate and given for general guidance. In the present invention, even if overall a relatively high temperature of from about 30° C. to about 40° C. is maintained during both primary and secondary drying, it is unlikely that a satisfactory moisture level (2% or less) will be produced by overall drying of less than about 20 hours.

As a result of our experimentation, we can now report that lyophilized preparations in accordance with the present invention have a content of decomposition products, A, B and C (as hereinafter defined) less than or equal to 3%, preferably less than or equal to 2%. Such lyophilized preparations have been shown to be stable for at least two years at 25°, provided that the moisture content is no greater than 2%. A sterile cake of this type is white or off white in appearance, and in consequence far more acceptable to a clinician than the material of U.S. Pat. No. 4963551.

The following Table 2 provides a comparison of lyophilization protocols in accordance with the present invention and the prior art process of U.S. Pat. No. 4963551. We have found that only by following the principles set out above, of which the parameter ranges in Table 2 are ranges indicative of preferred embodiments of the invention, can obtain a white or off-white cake of acceptable appearance and highly desirable low moisture content. Moisture content much higher than 2% has a deleterious effect on satability (there being an increased tendency to produce decomposition products A, B and C and, as mentioned in U.S. Pat. No. 4963551, a tendency to crystallize), and the moisture content should ideally be less than 1%. To achieve this latter desideratum an overall drying period (assuming a temperature of from about 30° C. to about 40° C. for both drying stages) of about 65 hours to about 80 hours is required for a 36 ml vial.

In table 2 it can be seen that when the vial size is 36 ml, the present process ideally requires a total drying time of over seventy hours at a 32° C. to 38° C. drying temperature.

When the vial size is 100 ml (as with prior art), a high operating temperature is still necessary despite the reduction in drying time.

TABLE 2

|  | Prior art 100 ml | Present invention 36 ml | Present invention 100 ml |
|---|---|---|---|
| Freezing | | | |
| Product temp (°C.) | −38 | −45°–54° C. | −45°—54° C. |
| Primary drying | | | |
| Product temp at end of period (°C.) | 10 | 32–38 | 32–38 |
| Duration of pr. dr. period (hrs) | 23 | 41–52 | 10–13 |
| Sec. drying | | | |
| Shelf temp ramp (°C./hr) | 1 | n/a temperature constant | n/a temperature constant |
| Duration temp ramp (hrs) | 20 | n/a temperature constant | n/a temperature constant |
| Production temp at end of sec. drying (°C.) | 27 | 32–38 | 32–38 |
| Duration (hrs) | 20 | 16–25 | 8–12 |
| Drying time under vacuum (hrs) | 43 | 73–80 | 24–30 |

Table 3 below gives details of further preferred Examples of the present inventive process. These are not limiting on the invention, but are merely illustrative.

hydrochloride salt. This can be achieved by freeze drying an HCl acid solution of ICRF-187.

A further aspect of the present invention is a therapeutic formulation of a salt of ICRP-187 with a therapeutically acceptable acid obtainable by reconstitution of a lyophilized preparation as defined above and which has a degree of coloration of no higher than Y4(Eur.Ph.).

The present lyophilized products generally have a dissolution time of less than about 1 minute, usually less than about 0.5 minutes when water is used for reconstitution purposes, the pH of a reconstituted hydrochloride product ranges from 1.4 to 1.8. Ideally the pH is about 1.5, at which pH about 90% of ICRF-187 is protonated. The resulting products are clear in appearance, and free of particulate matter.

In another aspect, the present invention provides the use of a means for screening light in protecting ICRF-187 from light-dependent decomposition. The screen can be any conventional screen known in the art, and generally is in the form of brown plastic or glass, eg a brown amber glass container meeting the specifications of <661>in USPXXII.

In general, drug clearance regulations do not accept the storage of new drugs in light resistant containers unless it has been shown that the drug in question is light sensitive. This is to ensure that clear vessels are generally employed, permitting visual inspection of product at all times. Hitherto, ICRF-187 has been stored in clear glass vessels without specific instructions for their storage in the dark. One extremely important aspect of the present invention is the finding of light sensitivity, and the requirement that this drug should now be stored in light resistant containers, such as

TABLE 3

|  | 1 | 2 | 3 | 4 | 5 | 6 | 7 | 8 |
|---|---|---|---|---|---|---|---|---|
| FREEZING STEP | | | | | | | | |
| Minimum product temperature (deg C.) | −65 | −56 | −60 | −60 | −58 | −61 | −60 | −55 |
| Time period product c-40 C. (hr:min) | 16:00 | 13:20 | 16:16 | 17:40 | 22:40 | 14:00 | 13:40 | 14:53 |
| SHELF TEMP R | | | | | | | | |
| Slope of ramp (degrees/hour) | 16.0 | 17.3 | 16.5 | 9.3 | 9.3 | 9.3 | 11.1 | 10.4 |
| Starting shelf temp (deg C.) | −60 | −60 | −65 | −48 | −38 | −42 | −50 | −46 |
| End shelf temp (deg C.) | 36 | 38 | 54 | 34 | 34 | 33 | 34 | 33 |
| Duration temperature ramp (hr:min) | 06:00 | 05:40 | 07:08 | 08:53 | 07:44 | 07:40 | 07:35 | 07:40 |
| PRIMARY DRYING | | | | | | | | |
| Shelf temp during primary drying | 35 | 35 | 35 | 35 | 35 | 33 | 34 | 33 |
| Condenser temperature | −70/−80 | −70/−80 | −70/−80 | −70/−80 | −70/−80 | −70/−75 | −70 | −70 |
| Maximum shelf temperature | 38 | 38 | 36 | 35 | 36 | 35 | 35 | 35 |
| Minimum product temperature | −28 | −28 | −36 | −25 | 34 | −24 | −25 | −24 |
| Maximum product temperature | 33 | 34 | 35 | 35 | 35 | 33 | 38 | 35 |
| Chamber pressure mbar; begin/end) | 0.05/0.01 | 0.06/0.02 | 0.06/0.04 | 0.20/0.02 | 0.20/0.02 | 0.20/0.07 | 0.20/0.05 | 0.20/0.05 |
| Duration Primary drying (hr:min) | 52:00 | 47:40 | 51:28 | 43:40 | 41:00 | 46:40 | 50:40 | 46:40 |
| SECONDARY DRYING | | | | | | | | |
| Shelf temp | 35 | 40 | 35 | 36 | 36 | 36 | 37 | 35 |
| Pressure rise test (ubar/150 sec) | 0.5 | 0.0 |  | 0.5 | 1.4 |  | 1.0 | 0.0 |
| Chamb. pressure end (ubar) | 5.5 | 2 | 3 | 2 | 2 | 15 | 16 | 20 |
| Duration secondary drying (hr:min) | 24:40 | 21:20 | 16:00 | 20:20 | 17:20 | 20:00 | 20:00 | 20:00 |
| TOTAL PROCESS | | | | | | | | |
| Drying time under vacuum | 75:40 | 74:40 | 73:19 | 78:00 | 67:20 | 75:20 | 79:20 | 77:20 |
| Total Process time | 96:40 | 92:00 | 92:52 | 110:40 | 90:00 | 95:20 | 97:40 | 98:20 |

One very important advantage of the present invention is that accelerated stability studies at 60° C. show that the present lyophilizated ICRF-187 preparations exhibit only a low degree of racemization under such conditions.

In the present invention, it is preferred that the lyophilized preparation of an ICRF-187 salt is in the form of the brown glass vessels. Furthermore, it is now clearly desirable that operations employed in the preparation and handling of ICRF-187 preparations and formulations should take place against a background of light-reducing/eliminating precautions.

The importance of moisture is emphasised by our finding that lyophilized ICRF-187 degrades to the same extent over time at 4° C. in the dark with 100 relative humidity as at 20° C. under light conditions with 45% relative humidity. In one experiment, we found that a significant decrease in the weight percent of ICRF-187 was observed under both sets of conditions after 55 days. At 20° C., a combination of humidity and light may be responsible for this, and an increase in moisture content of the sample to 7.5% within 55 days was observed. Under the 4° C. in the dark conditions only the high humidity can cause this degradation, and an increase in moisture content of the sample to 10.2% after 55 days of storage was seen. ICRF-187 clearly degrades in the dark very significantly under the influence of high humidity/moisture.

From the literature it is not known that ICRF-187 or salts, eg the hydrochloride salt, are light sensitive. The following Table 4 gives results of a controlled stability study we have performed showing that under the influence of light ICRF-187 hydrolyses more quickly than in the dark. After 57 days, although the content of ICRF-187 is still high, the color of the cake and the color of the reconstituted solution are unacceptable.

TABLE 4

| Time (days) | Total decomposition product % | | Decomposition products A + B % | |
|---|---|---|---|---|
| | Brown vial | Transparent vial | Brown vial | Transparent vial |
| 0 | 0.86 | 0.47 | 0.74 | 0.41 |
| 2 | 0.41 | 1.16 | 0.31 | 0.65 |
| 6 | 0.54 | 3.21 | 0.30 | 0.52 |
| 9 | 0.71 | 3.24 | 0.36 | 0.51 |
| 13 | 0.75 | 4.12 | 0.38 | 0.67 |
| 21 | 0.59 | 2.0 | 0.50 | 1.21 |
| 30 | 0.61 | 3.06 | 0.53 | 1.32 |
| 57 | 2.43 | 5.74 | 1.71 | 4.03 |
| Slope | | | 0.0249 | 0.0607 |
| intercept | | | 0.0928 | 0.0607 |
| r | | | 0.9381 | 0.9518 |

The results presented in Table 5 below show that, in addition to the fast formation of A and B, a highly colored decomposition product is also formed which results in a yellow colored cake.

Decomposition products A, B and C referred to above are open-ring compounds of the following structures:

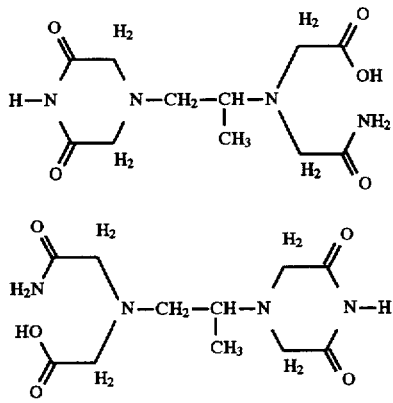

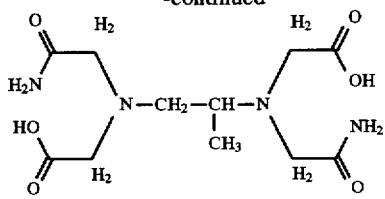

-continued

TABLE 5

| Time (days) | Appearance (colour cake) | | Colour of Solution | | Rate/extend of dissolution Clarity/Particles | | pm | |
|---|---|---|---|---|---|---|---|---|
| | 1 | 2 | 1 | 2 | 1 | 2 | 1 | 2 |
| 0 | white | white | B6 | Y6 | conform | conform | 1.60 | 1.64 |
| 2 | white | light yellow | Y5 | Y3 | conform | conform | 1.63 | 1.65 |
| 6 | white | yellow | Y6 | >Y1 | conform | conform | 1.60 | 1.61 |
| 9 | white | yellow | Y5 | >Y1 | conform | conform | 1.60 | 1.60 |
| 13 | white | yellow | Y5 | >Y1 | conform | conform | 1.60 | 1.60 |
| 21 | white | yellow | Y4 | >Y1 | conform | conform | 1.63 | 1.63 |
| 30 | white | yellow | Y4 | >Y1 | conform | conform | 1.52 | 1.61 |
| 57 | light yellow | yellow | Y2 | >Y1 | conform | conform | 1.63 | 1.62 |

(1) - brown glass vial,
(2) - clear glass vial.

Accordingly, the present invention also includes a process for preparing ICRF-187, such as set out or referred to above, during at least part of which precautions are taken to avoid light. Such a process can merely involve preparative process steps as described above or known in the art, or can just involve lyophilization techniques or reconstitution techniques, or any combination of any such steps/techniques; the important point is the taking of routine precautions against light.

The novel lyophilized preparations of ICRF-187 salts of the present invention can be formulated using any pharmaceutically acceptable acid to provide therapeutic formulations. Such acids include citric acid, phosphoric acid, hydrochloric acid and sulphuric acid. Dissolution time (based upon 20 mg of product in 1.0 ml of diluted acid) is preferably less than one minute, 20 seconds or so being desirable. Hydrochloric acid is the preferred acid because ICRF-187 is, we have found, soluble at an acceptable dissolution rate to produce a low pH solution (less than about 2.0). In contrast the rate of dissolution and the solubility of ICRF-187 in water or at pH 7.0 is limited, and stability at physiological pH is very limited.

The reconstituted formulations of the present invention are stable after reconstitution for at least 6 hours, which is quite adequate for clinical purposes. In fact at pH 1, ICRF-187 in solution seems to be stable for at least 2 days. At pH values higher than about 2, unstability of ICRF-187 solution progressively increases. We have found that reconstituted ICRF-187 formulations over longer periods of time show higher amounts of decomposition product A than of B and C regardless of light avoidance precautions. In general, light is a less important influence on stability for reconstituted formulations than the effect of the large amount of water present. This distinguishes from the relatively heightened importance of avoiding UV light in preserving lyophilized ICRF-187.

Other important aspects of the invention are:
a method for the treatment or prophylaxis of cancer, which method comprises administering an effective amount of the formulation of the invention; and a method for counteracting cardiotoxicity during drug therapy for the treatment or prophylaxis of cancer, which method comprises administering an effective amount of the formulation of the invention.

The present formulations are usable in clinical practice with dose levels of ICRF-187 of about 1000 mg/m² per dose, in accordance with practice known in the art. The following outlines an acceptable procedure for making up material for clinical use. It should not be construed, however, as limiting the invention, merely showing a preferred embodiment.

EXAMPLE

A lyophilized product is first prepared as below, and with reference to Table 6.

TABLE 6

Lyophilized Preparation

| Ingredients | Unit | Functions | standard |
|---|---|---|---|
| Active ingredient ICRF-187 | 500 mg | Active ingredient | |
| Other constitutents | | | |
| Concentrated hydrochloric acid (10N) | 0.25 ml | To acidify the ICRF-187 solution | Ph. Eur. |
| Water for injection | 24.75 ml | To dilute the hydrochloric acid | Ph. Eur. |
| Nitrogen | | Vials are closed under a nitrogen atmosphere | N.F./USP |

Each vial of lypholized ICRF-187 contains 500 mg of ICRF-187 as active ingredient, formulated as hydrochloride salt. The vials are prepared by dissolving ICRF-187 in 0.1N hydrochloric acid (at a concentration of 20 mg/ml of hydrochloric acid), sterilization of the fluid by filtration, filling of the vials with about 25 ml of the sterile solution, and lyophilization, in accordance with the inventive process as above.

Prior to use, the contents of the vials are dissolved in 25.0 ml of sterile water for injection (20 mg of ICRF-187 per ml), followed by neutralization with a specific volume of a sterile solution of 0.488M sodium hydrogen phosphate in water for injection (pH 9.1; the volume to be used depends on the dose to be administered) and dilution with a sterile solution of 0.9% sodium chloride in water for injection to a final volume of 200 ml, with a final pH of about 5.7. The final concentration in the infusion fluid is about 10 mg of ICRF-187 per ml.

The solution after reconstitution is acidic (pH 1.6), which results in higher stability. Because the compound has been shown to be sensitive to light, a brown glass, light-resistant vial is used.

In Table 7 below details are provided of the resulting product.

TABLE 7

ICRF-187 infusion fluid
The dose is calculated for a patient of 2.0 m² (1000 mg/m²)

| Product Characteristic | ICRF-187 |
|---|---|
| Dose | 2000 mg |
| Number of vials | 4 |

TABLE 7-continued

ICRF-187 infusion fluid
The dose is calculated for a patient of 2.0 m² (1000 mg/m²)

| Product Characteristic | ICRF-187 |
|---|---|
| Reconstitution | |
| solvent | water for injection |
| volume | 25.0 ml per vial |
| pH | 1.6 |
| concentration | 20 mg of ICRP-187 per ml |
| Dilution | |
| solvent | 0.448M Na₂HPO₄ pH 9.1 |
| volume | 20.0 ml |
| solvent | water |
| volume | 80.0 ml |
| Final | |
| volume | 200 ml |
| concentration | 10 mg of ICRF-187 per ml |
| pH | 5.7 |

We claim:

1. A process for producing a rapidly dissolving, pharmaceutically acceptable acid salt of ICRF-187 that is of a pharmaceutically acceptable color and appearance, said method comprising:

(a) lyophilizing an acidic aqueous solution of a pharmaceutically acceptable salt of ICRF-187, said solution having a concentration of ICRF-187 less than 25 mg/ml, said lyophilizing step comprising i) freezing said solution to a temperature of −45° C. to −65° C. to produce a frozen product, and ii) subjecting the frozen product to a primary drying stage lasting at least 30 hours to produce a sterile lyophilized cake of a pharmaceutically acceptable acid salt of said of ICRF-187, said lyophilized cake being white to off-white in color, crack-free, having a moisture content of 2% or less; and (b) protecting said lyophilized cake from light.

2. The process of claim 1, wherein the moisture content of the lyophilized cake is less than 1%.

3. The process of claim 1, wherein the concentration of ICRF-187 in said aqueous acid solution is less than 20 mg/ml.

4. The process of claim 1, wherein said primary drying cycle is between 30 and 75 hours.

5. The process of claim 4, wherein said lyophilizing step further comprises a secondary drying cycle of less than 25 hours.

6. The process of claim 5, wherein said secondary drying step is performed at a temperature from about 30° C. to about 40° C.

7. The process of claim 1, wherein the therapeutically acceptable acid salt of ICRF-187 is the hydrochloride salt.

8. The process of claim 1, wherein said lyophilized cake is protected from light by a light resistant container.

9. A process for producing a rapidly dissolving, pharmaceutically acceptable acid salt of ICRF-187 that is of a pharmaceutically acceptable color and appearance, said method comprising:

(a) lyophilizing an acidic aqueous solution of a pharmaceutically acceptable salt of ICRF-187, said solution having a concentration of ICRF-187 no greater than 25 mg/dl, said lyophilizing procedure comprising freezing said acidic aqueous solution to −45° C. to −65° C. and subjecting said frozen solution to a primary drying time of at least 30 hours, and a secondary drying time of no greater than 25 hours at 30° C. to 40° C., to produce a lyophilized cake of said pharmaceutically acceptable salt of ICRF-187 that is white to off-white in color, crack-free and that has a moisture content of less than 2%; and (b) protecting said white to off-white lyophilized cake from ultraviolet (uv) light.

10. The process of claim 9, wherein said moisture content of said lyophilized cake is less than 1%.

11. The process of claim 9, wherein said lyophilized cake of said salt of ICRF-187 contains less than 3 % of open-ringed decomposition products thereof.

12. The process of claim 11, wherein said lyophilized cake of said salt of ICRF-187 contains less than 2% of open-ringed decomposition products thereof.

* * * * *